United States Patent [19]

Brownlee et al.

[11] 4,142,533
[45] Mar. 6, 1979

[54] MONITORING SYSTEM FOR CARDIAC PACERS

[75] Inventors: Robert R. Brownlee, State College; G. Frank O. Tyers, Hershey; Paul H. Neff, Bellefonte, all of Pa.

[73] Assignee: Research Corporation, New York, N.Y.

[21] Appl. No.: 736,491

[22] Filed: Oct. 28, 1976

[51] Int. Cl.² ............................................. A61N 1/36
[52] U.S. Cl. .............................................. 128/419 PT
[58] Field of Search ..................... 128/2.05 R, 2.06 R, 128/2.1 A, 419 E, 419 P, 419 PG, 419 PS, 419 PT, 419 R, 421, 422, 423; 324/64; 340/255

[56] References Cited

U.S. PATENT DOCUMENTS

| | | | |
|---|---|---|---|
| 2,792,568 | 5/1957 | Scott et al. | 340/255 |
| 3,718,909 | 2/1973 | Greatbatch | 128/419 PT |
| 3,756,245 | 9/1973 | Thaler et al. | 128/419 PT |
| 3,768,014 | 10/1973 | Smith et al. | 128/419 PT |
| 3,774,619 | 11/1973 | Goldberg | 128/419 PT |
| 3,888,260 | 6/1973 | Fischell | 128/419 PS |
| 3,911,929 | 10/1975 | Gobeli | 128/419 PG |
| 3,920,005 | 11/1975 | Gombrich et al. | 128/419 PT |
| 4,021,736 | 9/1977 | Walters et al. | 128/419 PT |
| 4,041,954 | 8/1977 | O'Hara | 128/419 PT |

Primary Examiner—William E. Kamm
Attorney, Agent, or Firm—Cooper, Dunham, Clark, Griffin & Moran

[57] ABSTRACT

A complete system for telemetering and monitoring the functioning of an implanted pacemaker as well as controlling the testing of the functions from a remotely located central facility is disclosed specifically comprising the provision of capabilities for directly and simultaneously transmitting from the pacer, electrical signals indicative of multiple pacer functions, such as, pacer rate, cell voltage, refractory period, heart rate with pacer inhibited, R-wave level and sensing margin, sensing circuit and other component failure, cardiac electrode lead break, and hermetic integrity. The indicative signals are picked up at the patient's location for local analysis and/or telephonically communicated to a remote central monitoring station. The central station may control testing of the pacemaker functions by transmitting command signals back telephonically for coupling through cooperating external and implanted inductances or magnetically controlled switches to the implanted pacer circuitry.

19 Claims, 13 Drawing Figures

Fig. 8a.
PACER INHIBITED
NORMAL CARDIAC RATE

Fig. 8b.
PACER NOT INHIBITED
HI INTERFERENCE RATE

MONITORING SYSTEM FOR CARDIAC PACERS

BACKGROUND OF THE INVENTION

The present invention relates to systems for monitoring the performance of cardiac pacemakers and, more particularly, to a system within the implanted pacer for telemetering various functional parameters and a cooperating external system for sensing the telemetered information and presenting it in a read-out to the patient as well as transmitting it telephonically to a central monitoring station having means for analyzing and controlling the telemetering operation.

The telephone monitoring of pacemaker patients from centralized cardiac data centers has developed into a significant technology for improvement of patient safety. It is a particularly convenient means to determine the depletion of the pacemaker energy source so that elective reoperation can be performed prior to pacemaker failure. The remote monitoring systems presently in use transtelephone the pacemaker rate and the patient's ECG or peripheral pulse simultaneously to permit the determination of whether or not the patient's heart is responding properly to the pacemaker output pulse. The pacemaker's output pulse rate is usually made dependent upon its battery voltage so that the status of the battery can be determined from the patient's pulse rate. For the case of demand pacemakers that are inhibited by normal cardiac activity, remote monitoring requires assistance from the patient to induce a temporary pacemaker fixed rate mode. This procedure is accomplished by the patient's placing of an external permanent magnet over the pacemaker implant site. A magnetically operated reed switch within the pacemaker is employed to disrupt the normal cardiac sensing function and thereby force the pacemaker into a competitive fixed rate mode. Assessment of the battery voltage and pacemaker capture can be verified during the interval of the test.

While much progress has been made, it is still not possible with existing remote monitoring techniques, to assess the condition of the cardiac sensing threshold, the condition of the sensing circuitry, and a variety of vital timing functions. Additionally, the development of more complex pacemaker systems and functions has placed greater emphasis on the need to monitor the viability of these systems and functions.

Unfortunately, considerable restrictions are placed on remote pacemaker monitoring because of the required involvement of the patient. Patient skill, health, and safety are limiting factors in obtaining adequate remote tests of all vital pacemaker functions. Furthermore, with the development of advanced systems, the requirement for gathering adequate data during early clinical trials to prove efficacy prior to large scale marketing is limited by the techniques presently in use.

Advanced methods of monitoring vital pacemaker functions through the use of a special telemetry system contained within the implanted pacemaker are described in U.S. Pat. No. 4,026,305. That patent describes simple means to transmit data through the intact skin of the patient without requiring the use of the pacemaker pulse and/or patient pulse rate as the carrier of the information. By employing a patient pulse independent means to transmit the data, multiparameter monitoring at higher data rates is allowed and a larger number of vital functions can be kept under surveillance.

An object of the present invention is to provide an improved method and means that will allow a remote operator to command the monitoring tests to be performed in order to minimize both the test time and the involvement of the patient in the monitoring activity. Minimizing the test time and the patient involvement serves to reduce the hazards related to competitive fixed rate pacing and also reduces the potential for test errors due to the patient's lack of skill. The improved method and means are compatible with present methods of ECG and peripheral pulse monitoring, and the patient does not have to force his pacemaker to a fixed rate mode to assess implanted cell voltage as required in prior art.

SUMMARY OF THE INVENTION

In accordance with the present invention, the implanted pacemaker contains a telemetry system which monitors several vital pacing functions without interfering physiologically with the patient and which comprises transmitting circuitry, including an FM monitoring oscillator, and associated control circuitry which can be actuated to initiate selected tests in response to an external command. The external command may be provided by magnetic means which is manually or electrically operated for actuating internal magnetically responsive components such as reed switches or Hall effect devices, but preferably employs externally produced electrical command signals, which actuate an internal electrically operated switch, or switches. The command signals are coupled to the internal control circuitry from an external coil which cooperates with an internal coil in the pacer, or through a comparable antenna arrangement. A patient console is provided which contains instrumentation to process the monitored data which has been transmitted from the implanted device through the same, or another, internal-external coil or antenna arrangement. The console may include instrumentation to process ECG and pulse data as in prior art, as well as instrumentation to develop command control signals from signals received via telephone from a centralized data center and means to couple bidirectional data to the telephone system either acoustically or through directly connected electrical telephone couplers. The patient console may also contain metering for patient monitoring of cell voltage, either at the patient's convenience or in conjunction with a recharging schedule in the case of rechargeable pacemakers.

At the remote centralized data center an operator may direct the test sequence via a command console. The only involvement of the patient is to place a command-receive coil over the pacemaker implant site with one hand and to place a peripheral pulse sensor in the other hand. Conducting electrodes attached to these sensors are thereby placed appropriately from limb to limb so that both an ECG and peripheral pulse can be obtained as in prior art. However, a major difference between the prior art and the present invention is that the external coil placed over the pacer site serves as a transmitter of command signals to an implanted electrical switch for initiating the implant test functions, and as a receiver of data following each command function. Thus, both the test time and the test function are under the control of a trained operator.

Control functions are initiated by tone bursts under command of the operator of the control panel at the data center. The tone burst is telephone transmitted and received at the patient console where it is appropriately connected to the external coil and serves as a test command to the pacemaker by coupling through the internal coil. The implanted pacer control means contains appropriate internal signal filtering and detection to provide switch closure for actuation of a particular desired test. Multiple switches can be incorporated in the control means and the function test selection may be accomplished through the use of tone frequencies matched with appropriate tone filtering in a manner familiar to those skilled in the art. The tested function is monitored by the internal multiparameter monitor oscillator that sends a signal to the external coil via induction from the implanted coil. The monitoring oscillator can be an independant oscillator such as mentioned above or the main clock utilized to control event timing in digitally clocked pacemakers. The transmitted signal is amplified and processed within the patient console and sent via the telephone line to the data center as an FM modulated signal. At the remote center the data is processed in appropriate discrimination circuitry and subsequently converted to digital format for analysis, display, and storage. Any abnormalities encountered in the test may be formatted to indicate immediate physician consultation with follow-up of a hard copy print-out forwarded through the mail service.

In addition to the pacemaker test commands, the operator may signal the patient to pick up the telephone (PUP) or to indicate that the test is completed (EOT).

In accordance with the present invention, monitoring systems are provided in the pacemaker for telemetering: cell voltage, pacer rate; heart rate with the pacer inhibited; electrode lead break; sensing circuit and other component failure; hermetic integrity; refractory period; and R-wave level and sensing margin.

DETAILED DESCRIPTION OF THE INVENTION

Figure 1:
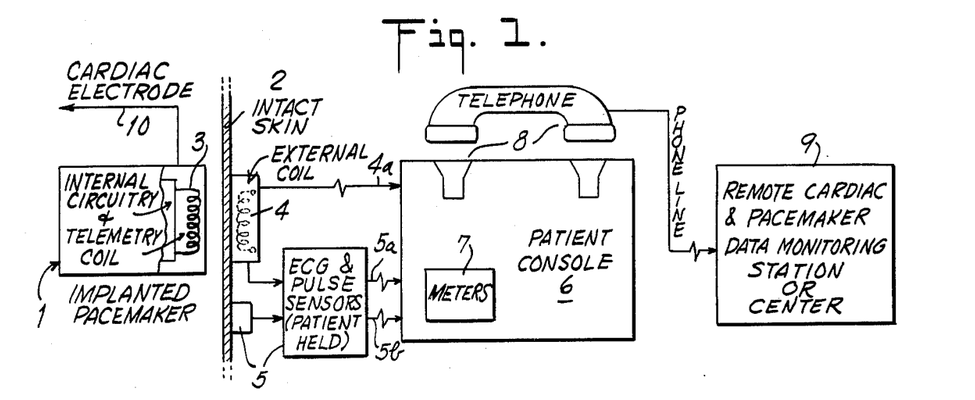
FIG. 1 is a diagrammatic illustration of a monitoring system in accordance with the present invention showing the major components and their relationship.

FIG. 1 shows the major components of a system in accordance with the present invention for monitoring the functioning of a pacemaker 1 implanted in a patient at an appropriate position under the skin 2. The pacemaker 1 contains electronic circuitry, as will be more fully described hereinafter, and a suitable transmitting means, such as a telemetry coil 3, for simultaneously transmitting signals out of the patient indicative status of multiple pacer operating parameters including the condition of the pacer cell, a variety of electronic components, the lead/electrode condition and hermetic integrity.

Externally the signals from the implanted pacemaker may be picked up by means of an external coil 4 held in the hand of the patient against the skin in the vicinity of the implanted coil 3. The coil 4 in combination with a peripheral pulse senscr 5, held in the other hand of the patient against the skin, and with conductive electrodes attached to these sensors, will pick up signals indicative of the pacemaker functioning and the patient's peripheral pulse and ECG. The combination of coil 4 and an indicator of cardiac rate, such as either the electrical ECG or peripheral pulse, will provide a determination as to whether the pacer pulse is stimulating the heart. This indicative data is fed for processing over lines 4a, and 5a and 5b (FIG. 1) to a patient console 6 which may be provided with appropriate meters 7 for patient viewing and a telephone coupling system 8 for transmitting the monitored data to a centralized cardiac data center 9. At the remote center 9 the monitored data transmitted by telephone can be processed through sophisticated analytical equipment for display, study, and storage, or in the event of any abnormalities, for immediate notification of the need for remedial action, as will be described more fully hereinafter.

Figure 2:
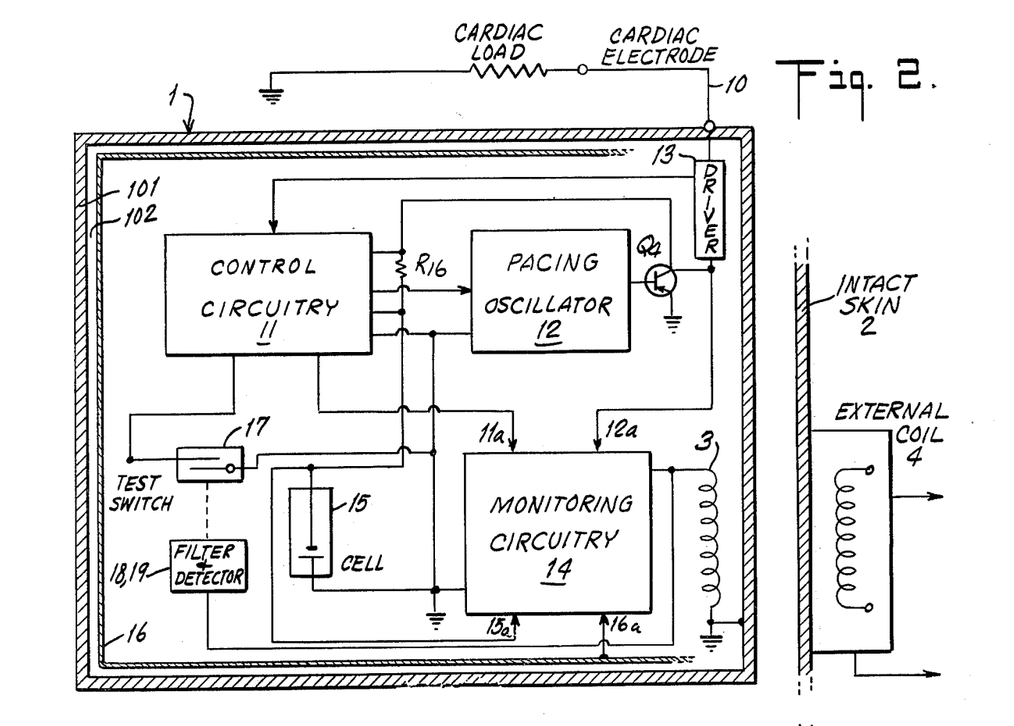
FIG. 2 is a block diagram of the major components contained within an implanted pacer in accordance with the present invention.

The major electronic components contained within the implanted pacemaker 1 are shown in FIG. 2. A cardiac electrode means 10 is connected to the heart of the patient and senses the electrical signals which affect the operation of the heart. These signals, in the form of P, Q, R, S and T waves familiar to the art, are transmitted by the electrode means 10 to the pacemaker 1 which processes them and, when required, produces an output of electrical pulses that are returned to the heart through the electrode means 10. Within the pacemaker 1 the electrical signals from the heart are fed to a set of control circuitry 11 which produces an output that controls a pacing oscillator 12. Pacing oscillator 12 produces an output of pacing pulses, at a fixed rate in accordance with the normal cardiac rate of about 70-80 beats per minute, which is communicated to the cardiac electrode means 10, through an output driver 13, for transmission to the patient's heart. In pacemakers of the demand type the output of the pacing oscillator 12 is inhibited by the output of the control circuitry 11 when the input signals from electrode means 10 are indicative of normal cardiac activity, that is, when the signals received contain a pulse rate and pulse spectral features in the range normally put out by the natural heart control pulses.

In accordance with the present invention, monitoring circuitry 14 is provided in the pacemaker, having an input 11a for receiving signals from the control circuitry 11 and an input 12a for receiving the pacing oscillator output. The circuitry 14, which may be in the form of an oscillator, produces its own output pulses in response to these signals which are transmitted out of the pacemaker by the telemetry coil 3. A suitable monitoring oscillator for use with the present invention is disclosed in U.S. Pat. No. 4,026,306. Alternatively, the basic clock in a digitally controlled pacemaker may be used, which clock would be dynamically modulated by the variety of monitored inputs herein described for assessing the various functions of the implanted pacemaker.

In addition to the other inputs to the monitoring circuitry 14, a power source in the form of a battery or cell 15 is included in the pacemaker and may provide an input 15a to the monitoring oscillator for telemetering the cell voltage as described in U.S. Pat. No. 4,026,305. A further input 16a is provided from an hermeticity or fluid leak sensing system 16 which will be described more fully below. Also, an externally-operable switching means 17 (shown in detail in FIG. 12), preferably operated in response to induced command signals is provided to initiate various tests of the functioning of the control circuits.

Figures 3, 4, 5:
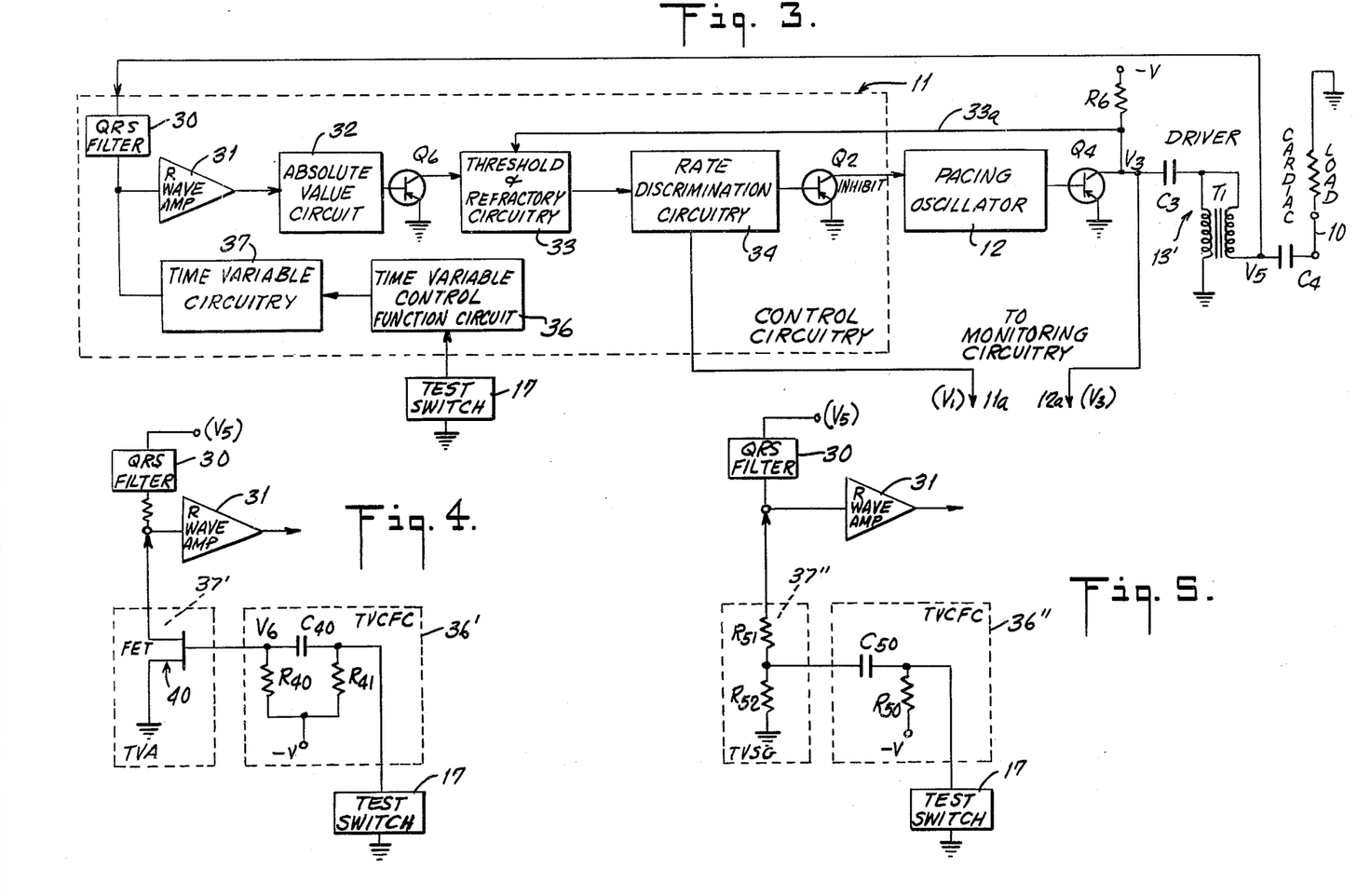
FIG. 3 is a block diagram showing in greater detail the operating components within certain of the major components shown in FIG. 2.
FIG. 4 is a schematic diagram showing one form of circuit for testing the fixed rate mode and the R-wave sensing margin when the pacer is in the inhibited state.
FIG. 5 is a schematic diagram of an alternate circuit for testing the fixed rate mode and the R-wave sensing margin when the pacer is in the inhibited state.

A typical general arrangement of the individual components included in the control circuitry 11 is shown in FIG. 3. These control function components, which sense the input from the cardiac electrode means 10 and the output of the pacing oscillator 12 and accordingly inhibit pacing oscillator operation, comprise: a QRS wave filter 30; an R-wave amplifier 31; an absolute value circuit 32; threshold and refractory circuitry 33 and rate discrimination circuitry 34.

Firstly, the QRS wave filter 30 is designed to filter out electromagnetic interference and the other wave spectra in the normal cardiac control signals and to pass the R-wave, the strongest of these signals, for controlling the inhibit function. The R-wave which is passed and amplified by R-wave amplifier 31 may be of dual polarity so that an absolute value circuit 32 is provided to convert the amplified input to a monopolarity or DC signal. The rectified signal is then received, through transistor $Q_6$, by the threshold and refractory circuitry 33 which senses the R-wave level and also introduces a refractory delay interval in its output to avoid multiple reset signals resulting from unwanted input signals, such as either cardiac generated or artifactual, following a paced beat. The resulting output of the threshold and refractory circuitry 33 is fed to rate discrimination circuitry 34 which ultimately controls the inhibiting of the pacing oscillator 12 through a transistor $Q_2$. The pacing oscillator 12 when uninhibited puts out a train of pulses of a fixed rate through transistor $Q_4$ to its output driver 13 which comprises, for example, capacitor $C_3$ and $C_4$ transformer $T_1$. Other driver means will also be found suitable as known to those familiar with the art.

It is also contemplated that the control functions may be alternatively arranged and may be in part digitally controlled timing functions that may be clocked from the monitoring oscillator or other suitable digital clock. In this regard it will be seen that the other variations of the system that are possible depend on the specific design selected for the control electronics. Specifically, if the control means are digital in nature, the digital waveforms can be utilized to drive the monitoring oscillator and, as mentioned previously, the monitoring oscillator can also be the main system clock frequency or derivative frequency that controls the various countdown functions required with digital mechanisms. It must be stressed that the average clock frequency can be maintained for adequate control of the fixed rate mode through countdown techniques even though dynamically modulated to carry vital information regarding the functioning of a variety of parameters.

The various monitoring capabilities of the system in accordance with the present invention will now be described.

Input refractory interval control and monitoring

During periods of bradycardia (slow heart beat), demand pacemakers revert to a fixed rate mode and in this mode require an input sensing refractory interval. The present invention is directed to a method utilizing the recharge interval of the pacemaker output driver capacitor as the control for the input refractory interval which method minimizes the complexity and parts count in the circuitry design for this purpose and facilitates monitoring of the function.

FIG. 3 depicts a general arrangement for the control and output components in such a demand or inhibited type pacemaker including the specific detail of suitable circuitry for the output driver 13.

When in operation, the pacing oscillator 12 normally provides pulses at a fixed rate of about 70 BPM. As will be seen in FIG. 3, the pulses from the fixed rate oscillator 12 saturate transistor $Q_4$ during the pulse period and rapidly discharge output driver capacitor $C_3$ causing the voltage at point $V_3$ to switch from $-V$ to ground. The resultant loop current through the transformer $T_1$ supplies energy, through capacitor $C_4$ and the cardiac electrode means 10, to the cardiac load. (It will be understood by those skilled in the art that alternate driver systems, which do not utilize a transformer, may require opposite polarity control.) When the oscillator-generated pulse ceases, transistor $Q_4$ shuts OFF and the voltage at point $V_3$ returns to $-V$. Thus, as long as oscillator 12 remains uninhibited, pulses at a fixed rate are supplied via cardiac electrode means 10 to the patient's heart.

Figure 6:
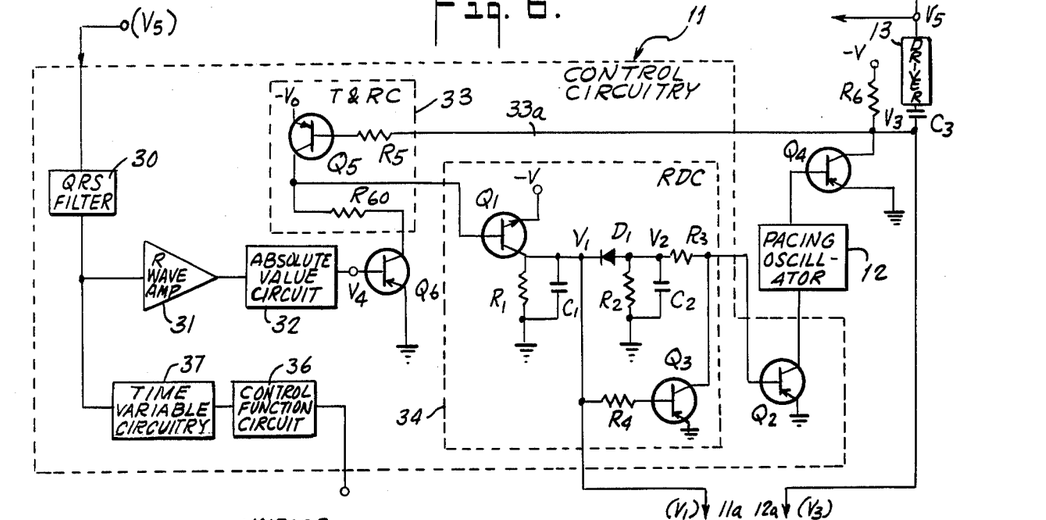
FIG. 6 is a schematic diagram particularly illustrating the pacer control circuitry in accordance with the present invention.
Figure 7:
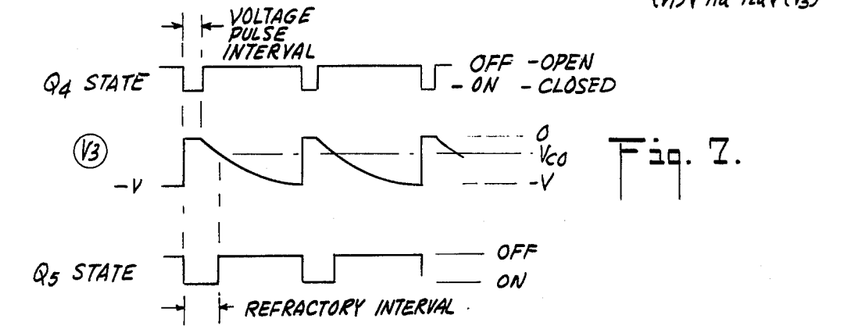
FIG. 7 is a timing diagram illustrating the recharge interval of the pacing oscillator output drive capacitor and its control of the input refractory interval.

Now, in accordance with the present invention, the voltage output pulses at point $V_3$, resulting from the oscillator pulses, are fed back to the threshold and refractory circuitry 33 via line 33a to act as a control therefor. Referring to FIG. 6, which shows the circuitry for the refractory control function in greater detail, it will be seen that transistor $Q_5$ in the threshold and refractory circuitry 33 is simultaneously switched ON from base drive via resistor $R_5$ by the input pulses on line 33a. The switching ON of transistor $Q_5$ shunts any signal arriving from the electrode input and thus provides the initiation of the sensing refractory interval with each delivered pacer output pulse. At the termination of each oscillator pulse, transistor $Q_4$ shuts OFF, and output driver capacitor $C_3$ begins to charge to $-V$ through input resistor $R_6$, according to the principal time constant $R_6C_3$. This charging is shown diagrammatically in FIG. 7 by the recharge shape of the voltage at $V_3$. It will be seen that the voltage at $V_3$ is adequate to maintain transistor $Q_5$ in the ON state, beyond the shutting OFF of transistor $Q_4$, until a cutoff voltage $V_{CO}$ is reached. Thus, the state of $Q_5$ provides the refractory gate interval, and the time constant $R_6C_3$ controls the magnitude of the refractory time. As compared to systems for this purpose in present commercial practice such as shown in U.S. Pat. No. 3,888,260, for example, the present system is extremely simplified.

The output of the threshold and refractory circuitry 33 (the $Q_5$ state) may be monitored by the monitoring oscillator 14 at the point $V_1$ in the rate discrimination circuitry 34 through line 11a as will be more fully explained below. As mentioned before, digitally controlled refractory waveforms can be likewise monitored employing the state waveform of the digital function. The following describes monitoring of analog RC discharge systems but is applicable also to digital waveforms by monitor observation of digital control state waveforms.

Rate discrimination control and monitoring

Rate discrimination circuits are employed in cardiac pacemakers to prevent pacer inhibition from high rate interference and as a side effect, during patient tachycardia (rapid heart action). The present invention involves a simple rate discrimination circuit that operates at low voltages, such as in single cell pacemakers, and that differs markedly from prior rate discriminators such as shown in U.S. Pats. No. 3,674,015 and No. 3,677,251. The present arrangement uses a dual memory circuit that is employed to control the inhibit function and control the packmaker escape interval. This dual memory circuitry allows simple adjustment of both the inhibition threshold rate and escape interval and the ready monitoring thereof. Digital countdown functions can also be employed in this rate discrimination circuitry.

The common functional configuration employed in demand pacemakers depicted in FIG. 3, takes into account the present improved form of rate discrimination circuit. The acutal circuitry for this purpose is shown in detail in FIG. 6. The performance of the rate discrimination circuitry 34 may best be understood by first considering the function of transistors $Q_1$, $Q_2$, and $Q_3$. Transistor $Q_1$, in the rate discrimination circuitry 34, is switched to an ON state coincident with the receipt of any signal (cardiac or noise) capable of traversing the preceding QRS filtering 30, and amplification, and refractory systems (31-33). Transistor $Q_2$, which receives an output from the rate discrimination circuitry 34, will inhibit and reset the pacing oscillator 12, whenever transistor $Q_2$ is switched to the ON state by base drive through resistor $R_3$. Transistor $Q_3$ prevents (shunts) any signals received by circuitry 34 from arriving at the base of transistor $Q_2$, when transistor $Q_3$ is in the ON state from base drive via resistor $R_4$. The three transistors are connected to the dual memory that makes up the remainder of the rate discrimination circuitry 34 and consists of two time constant circuits in the form of the resistor-capacitor combinations of $R_1C_1$ and $R_2C_2$ which are essentially isolated in function by diode $D_1$.

Figure 8A:
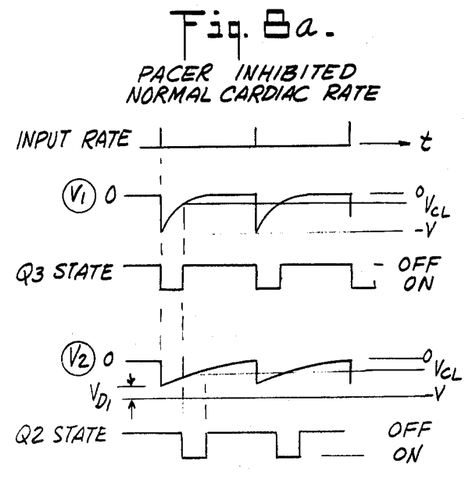
FIG. 8a is a timing diagram illustrating the operation of the rate discrimination circuitry when the input has a rate corresponding to the normal cardiac rate.

The circuit operation will now be described by considering two input rates. The first rate, illustrated graphically in FIG. 8a, characterizes the circuit operation during normal cardiac activity. It will be seen that coincident with a cardiac event (R-wave), transistor $Q_1$ will be turned On so that the voltage at the point $V_1$ in the circuit switches to $-V$, and the voltage at point $V_2$ switches to $-V$ less the voltage drop across diode $D_1$. When point $V_1$ switches to $-V$, transistor $Q_3$ is simultaneously turned ON from base drive via resistor $R_4$. With transistor $Q_3$ in the ON state, base drive to transistor $Q_2$ from point $V_2$ via resistor $R_3$ is shunted to ground thereby preventing transistor $Q_2$ from switching to the ON (inhibiting) condition. Following the input cardiac event, transistor $Q_1$ shuts OFF and the point $V_1$ begins to discharge toward ground according to the principal time constant $R_1C_1$. Resistor $R_4$ is also effective in the discharge of capacitor $C_1$ as long as transistor $Q_3$ remains ON. During this same period the point $V_2$ also begins to discharge toward ground according to the principal time constant $R_2C_2$. Resistor $R_3$ is also effective in discharging capacitor $C_2$ with transistor $Q_3$ in the ON state or for voltage levels above the $V_{BE}$ of transistor $Q_2$. Diode $D_1$ isolates the time constant circuits during the discharge condition. For normal cardiac rates, inhibition of pacing oscillator 12 is allowed to occur through choice of the ratio of the conposite time constants controlling the discharge of the points $V_1$ and $V_2$. By making the time constant controlling the voltage at $V_2$ considerably longer than the time constant controlling the voltage at $V_1$, a condition is reached in the timing cycle in which transistor $Q_3$ is allowed to switch OFF by virtue of the decay of the voltage at $V_1$ below its base drive conduction level $V_{CL}$. Transistor $Q_2$ is then allowed to be switched ON via resistor $R_3$ to inhibit and reset the pacing oscillator 12 by virtue of a sustained voltage at $V_2$ (see FIG. 8a). No pacer output is allowed to occur under this condition provided the input physiological cardiac interval is shorter than the escape interval of the system.

Figure 8B:
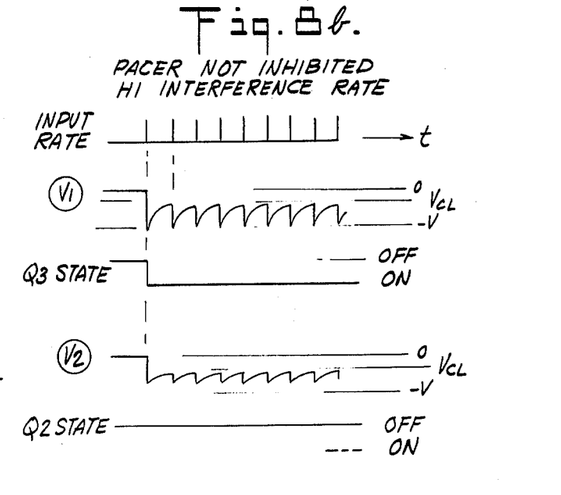
FIG. 8b is a timing diagram illustrating the operation of the rate discrimination circuitry when the input has a rate corresponding to a high interference rate.

The function of the system in the presence of high rate (non-inhibiting) signals is readily apparent from the same general reasoning. The high rate case is depicted graphically in FIG. 8b. For rapid input events, the principal time constant controlling the voltage at point $V_1$ prevents discharge of $V_1$ below the base drive conduction level $V_{CL}$ of transistor $Q_3$ via resistor $R_4$ so that transistor $Q_3$ remains ON thereby creating a continuous OFF state for transistor $Q_2$. As indicated, a continuous OFF state of transistor $Q_2$ prevents inhibiting of the pacing oscillator 12, and thus the pacemaker reverts to a fixed rate mode for input rates above normal physiologic inputs.

The threshold frequency above which inhibition cannot occur, for example, in the range from 300 to 500 BPM, is determined principally by the selection of the values of capacitor $C_1$, and resistors $R_1$, and $R_4$.

The escape interval of the system is controlled by the values of capacitor $C_2$, and resistors $R_2$, and $R_3$ in conjunction with the design escape rate of the pacing oscillator 12. In this system it is desirable for the basic escape interval of the pacing oscillator to be shorter than the "free run" fixed rate interval so that final adjustment of the desired system escape interval can be trimmed with $C_2R_2$. The escape interval following the reset of astable multivibrators generally employed as pacing oscillators can, for most types of circuits, be made shorter than the free run astable rate.

The voltage variations at the point $V_1$ may be sensed by the monitoring oscillator (14) through the input line 11a connected therebetween. This voltage then provides an active signal upon the detection of each cardiac contraction and provides the heart rate modulation signal to the telemetry system. The monitoring oscillator (14) telemeters the sensed data to the external monitoring system for processing and analysis so that the cardiac rate can be remotely monitored during periods of pacer inhibition. Also, the effects of the trimming or other adjustments to the components of the system, before and after implantation, can be monitored in this manner.

R-wave level and sensing margin monitoring

Demand (inhibited) cardiac pacemakers also generally include a method of testing the fixed rate mode when the pacemaker is in the inhibited state, that is, when there is no pulse output as a consequence of receiving a normal cardiac input signal rate. The fixed rate functional test serves to determine the viability of the pacing oscillator and capture of the ventricles, and is a means of determining the pacemaker cell voltage in rate-voltage dependent systems.

Usually only a few cycles of the fixed rate mode are required to perform all these functions. In fact, it is somewhat desirable to restrict the duration of the fixed rate condition to prevent undue extension of competition problems. The test is usually done by interrupting the R-wave inhibiting signal somewhere in the string of electronics leading to the inhibit control input to the pacing oscillator. The interruption test may be initiated non-invasively by actuating a switch within the pacemaker via an external control means such as a permanent magnet.

In conjunction with this prior art forced fixed rate test, certain methods have been devised in accordance with the present invention to test the R-wave level and/or R-wave sensing margin. The general scheme of these techniques is depicted in FIG. 3. Upon closure of an externally-controlled switch 17, by means of a system more fully described in connection with FIG. 12, a time variable control function, which may be analog or digital, is initiated by a time variable circuit 37 which may be either a time variable a signal generator 32 or time variable attenuator 37'. The circuit 37, if a signal generator, will serve to initially inhibit the R-wave signal by saturation of amplifier 31, and, if an attenuator, will cause R-wave attenuation.

In accordance with the present invention, for the latter case, employing a time variable attenuator, the attenuation ratio is modified to uninhibit the pacing oscillator 12 and the oscillator output is monitored through line 12a connected to point $V_3$. The time interval required to return pacing oscillator 12 to the inhibited state is measured by means of the output of the monitoring oscillator (14). With knowledge of the attenuation vs. time characteristic and sensitivity of the system, a measurement of the R-wave amplitude and sensing margin is derived from the duration of the fixed rate operation from the time of initial switch actuation to the return of the pacemaker to the inhibited state.

FIG. 4 depicts a simple system for achieving the attenuation method. In this particular embodiment the time variable attenuator 37' comprises a field effect transistor (FET) 40. Prior to the closure of the switch 17, the point $V_6$ is charged to the source voltage $-V$ and the FET 40 is "pinched off" preventing any attenuation of the R-wave signal to the amplifier 31, via QRS filter 30 and from the cardiac electrode means 10. Immediately upon closure of the switch 17, the voltage at point $V_6$ switches to ground potential, via capacitor $C_{40}$, so that the gate of FET 40 is switched to ground, a condition with defined very low ON resistance in some types of junction field effect transistors (Crystalonics CM640, for example). The R-wave signal is thus attenuated in proportion to the ratio between the resistances of filter 30 and the FET 40. Following switch closure, however, $C_{40}$ (and therefore point $V_6$) begins to recharge to $-V$ as a function of time constant $R_{40}C_{40}$. During the excursion of point $V_6$ from OV to $-V$ the resistance of the FET 40 varies over a range of from approximately 200 ohms to essentially infinite resistance, again on the condition that $-V$ is greater than the FET "pinch off" voltage. The resulting attenuation-time profile is then measured at point $V_3$ by the monitoring circuitry 14, and the output of the monitoring oscillator is used as indicated above to determine the R-wave amplitude and sensing margin.

FIG. 5 alternatively depicts a simple system for achieving the alternate signal generation method of inducing a time-variable offset voltage at the amplifier input that adds to or subtracts from the input R-wave amplitude to access the R-wave level and sensing margin. With this mechanism it is important to design the follow-on electronics in a manner that forces a fixed rate mode during saturation of the R-wave amplifier 31, a desirable feature for other reasons described herein with respect to lead break monitoring.

Immediately upon closure of the switch 17 in FIG. 5, a positive signal is injected into the amplifier input, via capacitor $C_{50}$ and resistor $R_{51}$, that sums with the R-wave signal from the cardiac electrode means 10. The resulting signal produces amplifier saturation and uninhibiting of the pacing oscillator 12. Following switch closure, as the $R_{52}$ side of $C_{50}$ returns to ground as a function of the composite time constant of the circuit, the R-wave eventually dominates, and the system returns to the inhibited mode. Again, knowing the time variable voltage character and the system sensitivity, the R-wave level and sensing margin can be determined from measurement of the duration that the pacemaker remains in the fixed rate mode. However, switch closure may provide only part of the answer, since R-wave signals are of dual polarity. Then, opening of the switch 17 provides the opposite polarity transient for a second observation of the time interval required for the pacer to return to the inhibited state. In this embodiment the alternate polarities of the test signals are useful to test the viability of both poles of the absolute value circuit since the transmission path through the absolute valve circuit depends on the input polarity.

Since the system of FIG. 5 allows saturation of the R-wave amplifier 31, amplifier viability and refractory delay times can be tested even in the absence of normal cardiac activity. The injected signal at the input of the R-wave amplifier serves as the test signal in the absence of cardiac activity and provides the modified modulation wave forms observable via the telemetry system in the same manner described for testing the R-wave level. DC coupling is essential for inducement of these tests as described in detail in the next section. These features are not presently found in current implantable pacemakers.

In final note, similar systems that allow continuous fixed rate operation during switch closure but provide the time variable test only on switch release are apparent through appropriate design of the time variable control function circuit 36. Continuous switch-controlled fixed-rate operation is desirable in some systems that are electromagnetic interference (EMI) inhibited.

DC coupling for monitoring

The importance of and advantages derived from the present invention in employing a DC coupled processing system for assessment of the R-wave amplifier viability, threshold circuit viability (during fixed rate pacing), and the measurement of the refractory sensing interval (under inhibited or fixed rate pacing conditions) will be seen by reference to FIG. 6.

FIG. 6 depicts the DC coupled system that allows these special monitoring capabilites. The DC coupling is stressed because of its importance in system transmission of a sustained, induced anomaly or failure anomaly so that the condition can be observed for a few cardiac (pacemaker) cycles via the monitoring system, or continuously during some types of failure modes.

The case of an induced test anomaly will be considered first. Closure of switch 17, as noted, provides a large saturating input signal via the time variable circuitry 36, 37 to the R-wave amplifier 31. This saturation condition drives the voltage at the point $V_4$ to its limit and, through transistor $Q_6$, resistor $R_{60}$, and transistor $Q_1$, the voltage at the point $V_1$ to its limit (if the switch is closed during a non-refractory condition). With an appropriate time constant for the time variable circuitry 36, 37 and cooperating circuitry in the QRS-wave filter 30, the amplifier 31 remains in saturation for several paced cardiac cycles as shown in the diagram in FIG. 9. Fixed rate pacing is forced if the initial condition present is an inhibited condition. The voltage at point $V_4$ remains at its limit during saturation and appears to the threshold and refractory circuit 33 as a long input event, similar to high level continuous interference. If the refractory function is viable, blocking of an input from point $V_4$ occurs during each pacer output triggered refractory interval (see FIG. 9). During the refractory interval then, $V_1$ returns to a blanked condition, 0V, according to the time constant in the cooperating rate discrimination circuitry 34. The cooperating rate discrimination circuitry is designed to view the situation as a high level continuous interference signal and thereby block transmission of inhibit signals during the test. This blocking is described more fully in connection with the operation of the rate discrimination control and FIG. 8b above. During the saturated amplifier condition the voltage at $V_1$ varies in the manner depicted on the left side in FIG. 9. The monitoring oscillator (14) receiving the voltage variations at $V_1$ through line 11a is modulated accordingly and thence transmits, via the modulation, a replica signal. If the induced condition continues for an appropriate number of paced cycles, the modulation waveform provides external monitoring of the parameters discussed.

Figure 9:
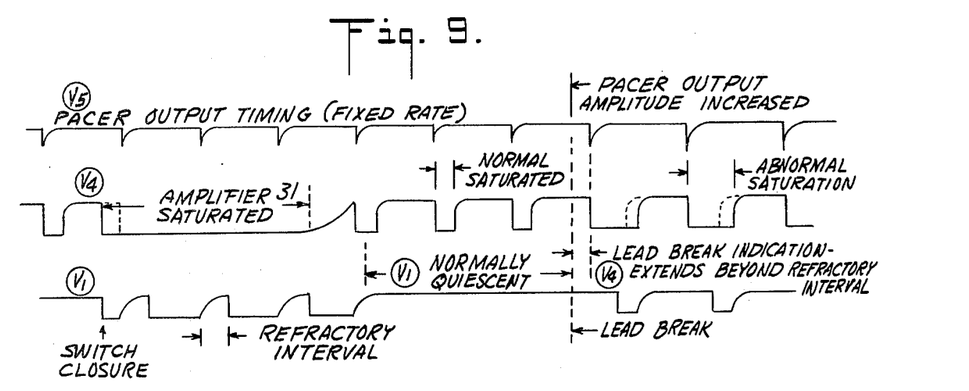
FIG. 9 is a timing diagram illustrating the pacer output for various test conditions.

Some fault modes are assessed by the monitoring oscillator (14) without switch actuation since an anomaly in the signal at $V_4$ from amplifier failure will result in a continuous anomaly in the signal at $V_1$ in view of the DC coupling. The voltage at $V_1$ appears saturated in the same manner as depicted in FIG. 9. All inclusive fault mode tests require switch actuation in order to determine if both poles of the absolute value circuit are operable. That is, both polarities of induced input signals are required to test the full viability of the absolute value circuit. A full understanding of how this is evaluated is within the purview of those skilled in the art so that the details are not discussed further here.

Lead break sensing is an additional fault mode that is monitorable by sensing an anomaly in the signal at $V_1$. The response of the system to a lead break is shown in the waveforms on the right side of FIG. 9. With the cardiac electrode means 10 disconnected, the pacer output level increases. The increased amplitude coupled with a modified discharge path for capacitors in the QRS-wave filter 30 results in extension of the R-wave amplifier saturation time following an output pulse. When the saturation time extends beyond the refractory interval, the system performs as though it received a cardiac signal immediately following the refractory interval. An inhibit (reset) pulse is supplied to the pacing oscillator 12 to generate a fresh escape interval. Following the new escape interval, the cycle repeats. The voltage at $V_1$ under these conditions is abnormal and the fixed rate interval is also extended. The abnormality will be telemetered by the monitoring oscillator (14) through line 11a and provide the appropriate indication to the external monitoring systems.

Hermeticity monitoring

The hermetic sealing of pacemakers has become an important feature in the art. However, currently available testing apparatus for initial verification of the hermeticity of a sealed container filled, as in the case of a pacemaker, with plastic such as epoxy, is sophisticated and expensive, and test results are frequently not well understood except when the sealed container is empty. Test results generally do not provide any prediction of duration of satisfactory hermetic sealing when organic materials and components that may absorb test gases are placed within the hermetic enclosure. Further, in critical situations such as in the pacemaker art, techniques for verification that body fluids have not entered a pacemaker during the years following its implantation presently do not exist, and it is important that any loss of hermeticity should be detected and the pacemaker replaced prior to loss of function.

Figure 10:
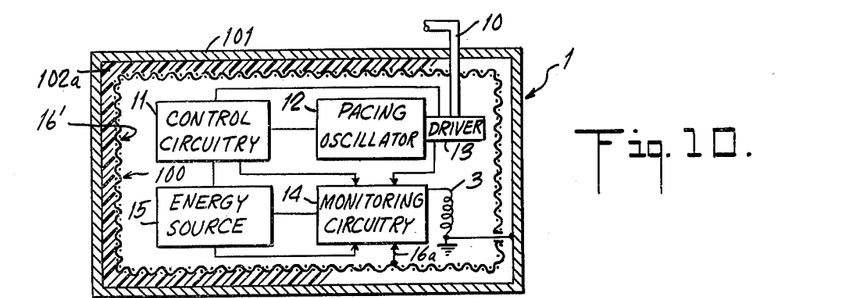
FIG. 10 is a diagrammatic illustration of a system for monitoring the integrity of the hermetic seal of the pacemaker in accordance with the present invention.

Accordingly, the present telemetry system, which as previously described, monitors the many pacemaker functions, can also be used to detect the entrance of conductive body fluids into the pacemaker casing. To this end, as shown in FIG. 10, an internal enclosure or envelope 100 is disposed in the pacer between the internal electronic components and the outer enclosure or casing 101. The envelope 100 is constructed of an electrically conductive material and may be in the form of a solid barrier sheet 16, such as indicated in FIG. 2, or in the form of wire mesh 16' such as indicated in FIG. 10. The pacer casing 101 is also constructed of an electrically conductive material and is preferably hermetically sealed so that no fluids would ordinarily enter the interior of the pacer. The space or gap 102, between the outer conductive casing 101 and the conductive barrier envelope 100, acts as an insulator and may be left empty or filled with a fluid-permeable insulative material or fabric 102a as shown in FIG. 10. The casing 101 is grounded and the conductive envelope 100 is connected to the monitoring circuitry 14 through the line 16a. With this arrangement should a fluid or electrolyte leak from the environment external to the previously hermetically sealed device and bridge the insulating gap 102, electrical contact will be made thereby between the envelope 100 and the outer casing 101. Such contact may be used to shift the output frequency of the monitoring oscillator (14) to a warning zone that will indicate loss of hermeticity. A suitable warning signal indicating hermetic failure may be read out on the external display apparatus employed to monitor all of the telemetered pacemaker parameters. It will also be seen that this arrangement may be used in conventional pacemaker systems without special monitoring apparatus by using its output to cause a benign shift in the frequency of the pacing rate of such pacers. In this latter case the fixed pacing rate of the conventional system would then be observed to determine hermetic failure prior to absolute system failure in a manner similar to that now used to assess cell depletion.

It will be seen that if the conductive envelope 100 is a solid sheet, as shown in FIG. 2, it may act as an inner hermetic seal for the encapsulated electronics and thus give ample warning of loss of hermetic integrity long before the pacemaker function is lost. With any envelope configuration, the arrangement will not only warn against impending pacemaker function loss due to failure of hermetic sealing, but also permits the testing of hermeticity in a pressurized conductive fluid prior to biological implantation during the manufacturing process. This added monitoring capability therefore may be incorporated into the present telemetering system simply and inexpensively as shown or can be added as a benign modifier of the fixed pacing rate in systems of current design.

Telemetered information sensing, analyzing and control system

Figure 11:
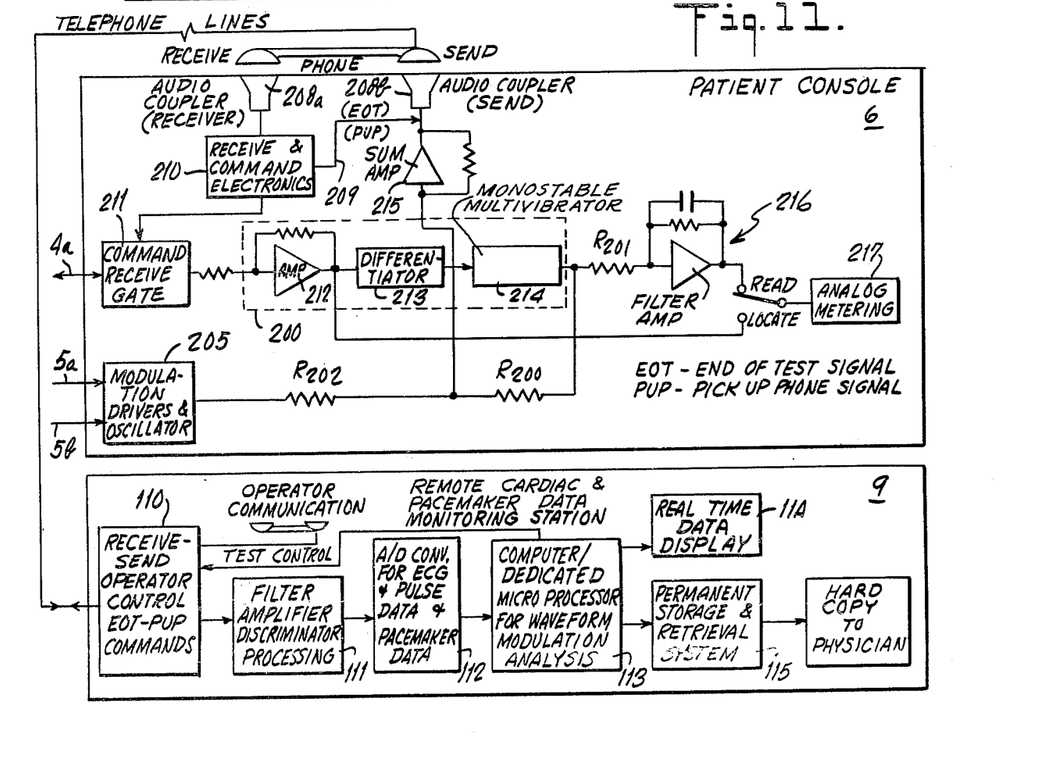
FIG. 11 is a block diagram illustrating in greater detail the components of the external monitoring system shown in FIG. 1.

FIG. 11 shows in greater detail the internal components of one functional embodiment of the external monitoring system shown in FIG. 1. This system is particularly adapted to permit a remote operator to command the monitoring tests to be performed and analyzed. The patient console 6 which may be located either at a patient's home or in a physician's facility, when coupled with the conventional telephone network, may be used to receive, generate and transmit data and control signals between the patient and centralized remote data monitoring station 9.

More particularly, a test operator located at the central data monitoring station 9 may control the test command signals to be transmitted over the telephone by means of a send-receive operator control panel 110. Tone bursts commands with an appropriate frequency and code for transtelephone communication are initiated by the operator and are sent to and received in receive-command electronics 210 within the patient console 6. The command signals control both the initiation of command functions for transmission to the pacemaker 1 and signal reception from the pacemaker by operating a bi-directional command-receive gate 211. When a test signal command is transmitted through the electronics 210 and gate 211, the gate 211 will then allow the passage of signals received from the pacemaker for processing to discrimination circuitry 200, comprising, for example, an amplifier 212, differentiator 213, and monostable multivibrator 214. The output of this discrimination circuitry 200 in the form of an FM modulated signal is fed to a summing amplifier 215, through a resistor $R_{200}$, for transmission over the telephone lines to the receive-send operator control panel 110 at the central monitoring station 9. The output may also be sent through a resistor $R_{201}$ for discriminator filtering in circuitry 216 and display upon a meter 217, or system of meters, to permit immediate patient monitoring of certain important functions such as pacemaker energy source condition, and hermeticity integrity, etc.

The signals received over lines 5a and 5b from the ECG and pulse sensors 5 are processed through modulation drivers and oscillator circuitry 205 and fed, through a resistor $R_{202}$, also to the summing amplifier 215 for telephone transmission to the central monitoring station 9. Additional patient display of peripheral pulse and ECG data may be accordingly added to the patient console in a manner within the purview of those familiar with the art.

The FM data received over the telephone at the remote monitoring station 9 is fed to a filtering network 111 for discrimination detection and then to analog-to-digital processing circuitry 112 for conversion to digital format. The digitized signal is then sent to a suitable computer or dedicated microprocessor 113 that is programmed to analyze the data to determine normal or abnormal functioning of the pacemaker from the monitored parameters. Immediate data presentation to the operator may be produced on a real time data display 114 and/or the data may be permanently stored in a storage and retrieval system 115. Thus all the monitoring information is made available for record keeping at the data center and for ultimate communication to the patient's physician. If a condition is monitored requiring immediate attention, the operator may signal the patient to pick up the telephone by means of a coded PUP tone which will be received by the audio receiver coupler 208a and fed from the receive-command electronics 210 via line 209 to the audio-send coupler 208b. The same line 209 may carry the end of tests (EOT) signal to indicate the end of the monitoring. The patient may on his own make daily or weekly observations on the patient console meter 217 of the major vital functions to ensure early warning of impending malfunction.

The use of an appropriate FM modulating signal for telemetering from the pacemaker also permits the patient to provide data to the remote central monitoring station when the patient console is inoperative, or when he is away from home, through the use of a conventional AM transistor radio. The transistor radio may be substituted for the patient console 6. The radio antenna may be used to pick up the telemetered data and the speaker can broadcast the data into the telephone for transmission to the data center.

Figure 12:
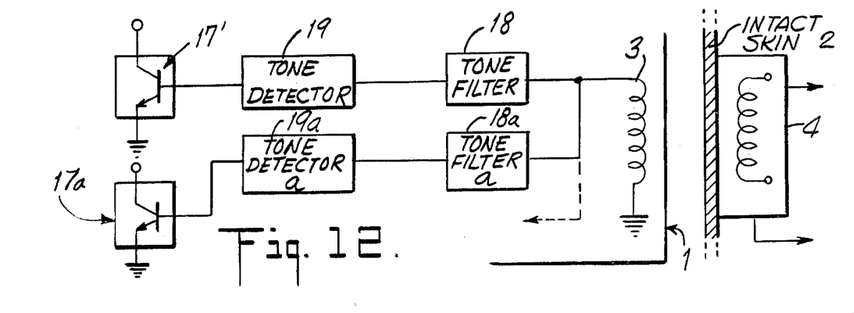
FIG. 12 illustrates a switching system in the implanted pacer which is operable in response to externally induced command signals to initiate various tests of the functioning of the control circuits.

One embodiment for operating the test initiating switch 17 by means of externally produced electrical command signals is shown in FIG. 12. The command signal, for example, in the form of a tone burst, which may be communicated telephonically from the centralized cardiac data center 9 or locally produced in the patient console 6, is fed to a send coil or antenna in the patient console or preferably to the external coil 4. The signal is thereby coupled to the telemetry coil 3, or another implanted coil, which is connected to switch 17 through appropriate signal filtering and detection components. More particularly, the filtering component 18 may be in the form of a narrow band filter which passes the particular frequency of the tone burst and the detection component 19 may be a rectifier for providing a DC input to the switch 17 which is in the form of a switching transistor 17'. If desired, one (18a, 19a, 17a) or more tone filter, tone detector and switching transistor systems may be respectively provided in parallel with the initial system (18, 19, 17) to permit the selective initiation of different tests using command tone bursts of different appropriate frequencies.

In summary, it will be seen that with the present invention it is possible for the implanted monitoring circuitry to telemeter such functions as the pacer rate through input 12a; the cell voltage through input 15a;

hermetic integrity through input 16a; and other pacer parameters such as refractory period, heart rate during periods of pacer inhibition, R-wave level and sensing margin, and malfunctions such as in the R-wave sensing circuit, cardiac electrode lead break and other component failures through input 11a. The telemetered data is picked up by the external monitoring system which may analyze and present it at the patient's location and/or transmit it telephonically to a central facility for analysis and storage. The central monitoring station is provided with means to control certain of the telemetering operations by transmitting test command signals back through the system to the implanted circuitry, thus minimizing patient involvement.

We claim:

1. Apparatus for remotely monitoring and controlling the functioning of a cardiac pacer implanted in a patient, said apparatus comprising:

telemetering means in said implanted pacer for telemetering a modulated electrical signal simultaneously indicative of multiple pacer parameters related to the functioning thereof and comprising:
  first inductance means for electrically transmitting said modulated signal out of said pacer patient;
  control circuitry means for controlling the output of said pacer to the heart of the patient in response to R-waves received from said heart and comprising:
    time variable circuitry means for interrupting said R-waves to, and thus producing a test mode in, said control circuitry means;
    means for producing signals indicative of the functioning of said control circuitry means when said control circuitry means is in the test mode; and
    junction means for receiving said functioning indicative signals;
  monitoring circuitry means, connected between said junction means and said first inductance means, for producing said modulated signal with a simultaneous multiparameter indicative modulation thereon and feeding it to said first inductance means, said modulation including a parameter indicative component in response to the receipt of, and related to, said functioning indicative signals from said junction means; and
  switching means responsive to an externally produced command signal for actuating said time variable circuitry means whereby said signals indicative of the functioning of said control circuitry means are communicated to said monitoring circuitry means and produce a related parameter indicative modulation on said modulated signal which is fed to said first inductance means for transmission thereby as said telemetered signal; and
means external to said patient for monitoring said telemetered signal comprising:
  second inductance means for receiving said telemetered signal from said first inductance means;
  means operatively connected to said second inductance means for analyzing the modulation on said telemetered signal received by said second inductance means; and
  means for producing a command signal to actuate said switching means to put said control circuitry means in said pacer in the test mode.

2. Apparatus as in claim 1 wherein said pacer comprises a cardiac electrode lead for conducting said pacer output to the patient's heart and said telemetering means further comprises means connected to said control circuitry means for supplying a signal indicative of a break in said cardiac electrode lead thereto, and in response to which break signal said monitoring circuitry means produces a related parameter indicative modulation on said modulated signal to said first inductance means.

3. Apparatus as in claim 1 wherein said pacer comprises an hermetically sealed casing and said telemetering means further comprises means connected to said monitoring circuitry means for producing a signal indicative of the breakdown of hermetic integrity of said casing in response to which breakdown signal said monitoring circuitry means produces a related parameter indicative modulation on said modulated signal to said first inductance means.

4. Apparatus as in claim 1 wherein said control circuitry means further comprises an electronic circuit component and said functioning indicative signal producing means produces signals indicative of the failure of said electronic circuit component.

5. Apparatus as in claim 1 wherein said control circuitry means further comprises means for producing a refractory period and said junction means picks up signals indicative of said refractory period and said monitoring circuitry means produces a related parameter indicative modulation on said modulated signal in response thereto.

6. Apparatus as in claim 1 wherein said control circuitry means further comprises means for sensing the cardiac R-waves of the heart of said patient and said functioning indicative signal producing means produces signals indicative of the sensing margin of said R-wave sensing means.

7. Apparatus as in claim 1 wherein said control circuitry means further comprises means for sensing the cardiac R-waves of the heart of said patient and said functioning indicative signal producing means produces signals indicative of the level of the R-waves sensed.

8. Apparatus as in claim 1 wherein said pacer comprises means for producing pacing pulses and said telemetering means further comprises means for supplying signals indicative of the rate of said pacing pulses to said monitoring circuitry means which produces a related parameter indicative modulation on said modulated signal in response thereto.

9. Apparatus as in claim 1 wherein said switching means further comprises:
  means connected to said first inductance means for filtering said command signal;
  means connected to said filtering means for rectifying said filtering signal; and
  means connected to said rectifying means and said time variable circuitry means and responsive to said rectified signal for actuating said time variable circuiry means and initiating said test mode in said pacer.

10. Apparatus as in claim 1 wherein said first inductance means is operatively connected to said switching means; and said external means further comprises means for applying said command signal to said second inductance means for transmission to said first inductance means to thereby actuate said switching means.

11. Apparatus as in claim 1 wherein said monitoring means further comprises means for displaying the output of said analyzing means.

12. Apparatus as in claim 1 wherein said monitoring means further comprises:
  means for transmitting the output of said analyzing means to a location remote from said patient.

13. Apparatus as in claim 12 wherein said command signal producing means comprises means disposed at said remote location for communicating a command signal to said analyzing means output transmitting means for transmission to said analyzing means.

14. Apparatus as in claim 13, wherein said analyzing means further comprises means for applying said command signal to said second inductance means.

15. Apparatus as in claim 1 wherein said control circuitry means further comprises means for input rate discrimination and means connected to said junction means for supplying signals indicative of the operation of said rate discrimination means to said monitoring circuitry means which produces a related parameter indicative modulation on said modulated signal in response thereto.

16. Apparatus as in claim 15 wherein said input rate discrimination means comprises:

means for conducting an electrical output;

a first time constant circuit;

means connected to said first time constant circuit for providing an electrical input thereto;

a second time constant circuit having a time constant which is longer than that of said first time constant circuit and connected to said output conducting means;

a diode connecting said first time constant circuit and said second time constant circuit; and shunting means connected between said first time constant circuit and said output conducting means for shunting said second time constant circuit and connected to said junction means.

17. Apparatus as in claim 1 wherein said pacer comprises electrode means for conducting electrical signals including cardiac R-wave signals from and cardiac pacing pulses to the heart of the patient, and said control circuitry means further comprises means for sensing the electrical signals conducted by said electrode, and said time variable circuitry means comprises means for attenuating the electrical signals sensed by said sensing means.

18. Apparatus as in claim 17 wherein said attenuating means comprises:

a FET connected between said sensing means and ground; and means for producing an input to said FET to produce an input to said sensing means.

19. Apparatus as in claim 17 wherein said switching means further comprises means for initiating the operation of said attenuating means.

* * * * *

UNITED STATES PATENT AND TRADEMARK OFFICE
CERTIFICATE OF CORRECTION

PATENT NO.  : 4,142,533
DATED       : March 6, 1979
INVENTOR(S) : Robert R. Brownlee et al.

It is certified that error appears in the above-identified patent and that said Letters Patent are hereby corrected as shown below:

Fig. 4, the resistor between components 30 and 31 should be deleted and the lead line from "37'" should be solid rather than dotted.

Fig. 5, the lead line from "37"" should be solid rather than dotted;

Col. 4, line 21, "indicative" should read --indicative of the--.

Col. 5, line 15, "4,026,306" should read --4,026,305--.

Col. 9, line 38, delete "a", second occurrence

Col. 10, line 6, "OV" should read --0V--;
         line 48, "valve" should read --value--.

Claim 9, line 6, "filtering" should read --filtered--;
         line 9, "circuitry" should read --circuitry--.

Claim 13, line 4, "transmittingmeans" should read --transmitting means--.

Signed and Sealed this

Tenth Day of July 1979

[SEAL]

Attest:

LUTRELLE F. PARKER

*Attesting Officer*   *Acting Commissioner of Patents and Trademarks*